US 6,495,039 B1

(12) United States Patent
Lee et al.

(10) Patent No.: US 6,495,039 B1
(45) Date of Patent: Dec. 17, 2002

(54) SYSTEM FOR IN-LINE FILTERING BIOLOGICAL LIQUID

(75) Inventors: Eric K. Lee, Acton, MA (US); Franco Castino, Sudbury, MA (US)

(73) Assignee: Whatman Hemasure, Inc., Marlborough, MA (US)

( * ) Notice: Subject to any disclaimer, the term of this patent is extended or adjusted under 35 U.S.C. 154(b) by 0 days.

(21) Appl. No.: 09/605,002

(22) Filed: Jun. 27, 2000

Related U.S. Application Data

(62) Division of application No. 09/296,882, filed on Apr. 22, 1999, now Pat. No. 6,123,859.
(60) Provisional application No. 60/082,670, filed on Apr. 22, 1998.

(51) Int. Cl.[7] .............................................. B01D 36/00
(52) U.S. Cl. .................... 210/257.1; 210/130; 210/136; 210/143; 210/252
(58) Field of Search ................................. 210/130, 136, 210/252, 257.1, 420, 143; 604/406, 408, 410

(56) References Cited

U.S. PATENT DOCUMENTS

| 4,447,230 A | 5/1984 | Gula et al. .................... 604/122 |
| 4,551,131 A | 11/1985 | Miles et al. .................... 604/31 |
| 4,596,657 A | 6/1986 | Wisdom ....................... 210/206 |
| 4,680,025 A | 7/1987 | Kruger et al. .................. 604/6 |
| 4,846,787 A | 7/1989 | Aall-Flood et al. ............. 604/5 |
| 4,915,848 A | 4/1990 | Carmen et al. .............. 210/749 |
| 4,919,823 A | 4/1990 | Wisdom ....................... 210/749 |
| 4,985,153 A | 1/1991 | Kuroda et al. ............... 210/782 |
| 4,997,577 A | 3/1991 | Stewart ........................ 210/767 |
| 5,098,371 A | 3/1992 | Juji et al. ........................ 604/4 |
| 5,128,048 A | * 7/1992 | Stewart et al. ........... 210/257.1 |
| 5,180,504 A | 1/1993 | Johnson et al. ............. 210/767 |
| 5,269,946 A | 12/1993 | Goldhaber et al. ......... 210/767 |
| 5,378,229 A | 1/1995 | Layer et al. ................... 604/31 |
| 5,405,343 A | 4/1995 | Mohr ......................... 605/416 |
| 5,536,412 A | 7/1996 | Ash .............................. 210/645 |
| 5,601,730 A | 2/1997 | Page et al. ................... 210/806 |

FOREIGN PATENT DOCUMENTS

| CA | 737249 | 6/1966 |
| WO | WO83/00813 | 3/1983 |

* cited by examiner

*Primary Examiner*—John Kim
(74) *Attorney, Agent, or Firm*—Candice J. Clement, Esq.; Heslin Rothenberg Farley & Mesiti, P.C.

(57) ABSTRACT

An in-line biological liquid filtration system and method comprises a collection container for receiving biological liquid. A filter is located downstream of the collection container and in fluid flow communication therewith. A storage container for receiving filtered biological liquid is located downstream of the filter and the storage container is in fluid flow communication with the filter and with the collection container. An additive solution is located in the storage container. At least one automatic control member automatically restricts a flow of biological liquid or additive solution when flowing the liquid or solution between the collection container and the storage container.

8 Claims, 3 Drawing Sheets

SYSTEM FOR IN-LINE FILTERING BIOLOGICAL LIQUID

This application is a divisional application of U.S. Ser. No. 09/296,882 filed Apr. 22, 1999 now U.S. Pat. No. 6,123,859; which claims the priority of U.S. provisional application No. 60/082,670 filed Apr. 22, 1998, both of which are incorporated fully herein by reference.

FIELD OF THE INVENTION

This invention relates generally to filtering a biological liquid. More specifically, this invention comprises an automatic gravity driven in-line filtration system and method for filtering a biological liquid such as blood or blood product to remove leukocytes therefrom.

BACKGROUND OF THE INVENTION

Various blood filtration systems exist in the prior art. However, of the systems that are in-line filtration systems, these require user manipulation of valves and/or mechanically driven components during the filtration process. The manipulation of valves must take place at the proper time during the filtration process or the system will not filter properly and the blood being filtered may be rendered unusable. The use of mechanically driven components requires additional utility hook ups and complicates the overall system. Since systems including user manipulation of valves and mechanically driven components are more time dependent, use restrictive and costly, it is desirable to achieve a liquid filtration system which may filter blood without the manipulation of valves or the use of mechanically driven components.

Additionally, it is desirable to obtain a system wherein an additive storage solution is located remotely from a whole blood collection container. As will be described in greater detail hereinafter, the features of the present invention differs from those previously proposed.

SUMMARY OF THE INVENTION

The shortcomings of the prior art may be alleviated using a filtration system constructed in accordance with the principles of the present invention. The present invention comprises a process for filtering a biological liquid in an in-line filtration system. The process may comprise the following steps: providing the biological liquid in a collection container; conveying an additive solution into the collection container to mix with the biological liquid wherein the additive solution is located in a storage container and is automatically restricted to flow in a fluid path substantially bypassing a filtration media, the filtration media being disposed between the collection container and the storage container; mixing the biological liquid and the additive solution to form a mixture; and conveying the mixture into the storage container wherein the mixture is automatically restricted to flow in a second fluid path substantially passing through the filtration media.

According to the present invention there is also provided an in-line biological liquid filtration system. The system preferably comprises the following. A collection container for receiving biological liquid. A filter located downstream of the collection container and in fluid flow communication therewith. A storage container for receiving filtered biological liquid located downstream of the filter, the storage container in fluid flow communication with the filter and with the collection container. An additive solution located in the storage container. And, at least one automatic control member automatically restricting a flow of biological liquid or additive solution between the collection container and the storage container.

Another feature of the invention relates to a process and system for providing a collection container that is substantially free of any additive solution before and while biological liquid is collected in the container. Further, the additive solution is preferably located remotely in another container that serves as both a storage container for the additive solution prior to using the system and then as a long term storage container for biological liquid, preferably comprising blood or blood product, after the liquid is filtered through the system.

Still other features of the invention concerns the use of multiple storage containers and processes for separating and filtering the biological liquid, means for sampling collected liquid and an automatic, gravity operated, closed in-line filtration system.

In accordance with the following, it is an advantage of the present invention to provide an easy to use, closed in-line filtration system that can operate automatically merely under the force of gravity with minimum user supervision and without mechanical component manipulation.

A further advantage is to provide an invention that can be used with conventional liquid separation techniques, such as a centrifuge, without breaching the integrity of the closed system and while enabling multiple separation steps and storage containers for blood and blood products.

DESCRIPTION OF THE DRAWINGS

Other features and advantages of the invention will become more readily apparent upon reference to the following description when taken in conjunction with the accompanying drawings, which drawings illustrate several embodiments of the invention.

DETAILED DESCRIPTION OF THE PREFERRED EMBODIMENT

Figure 1:
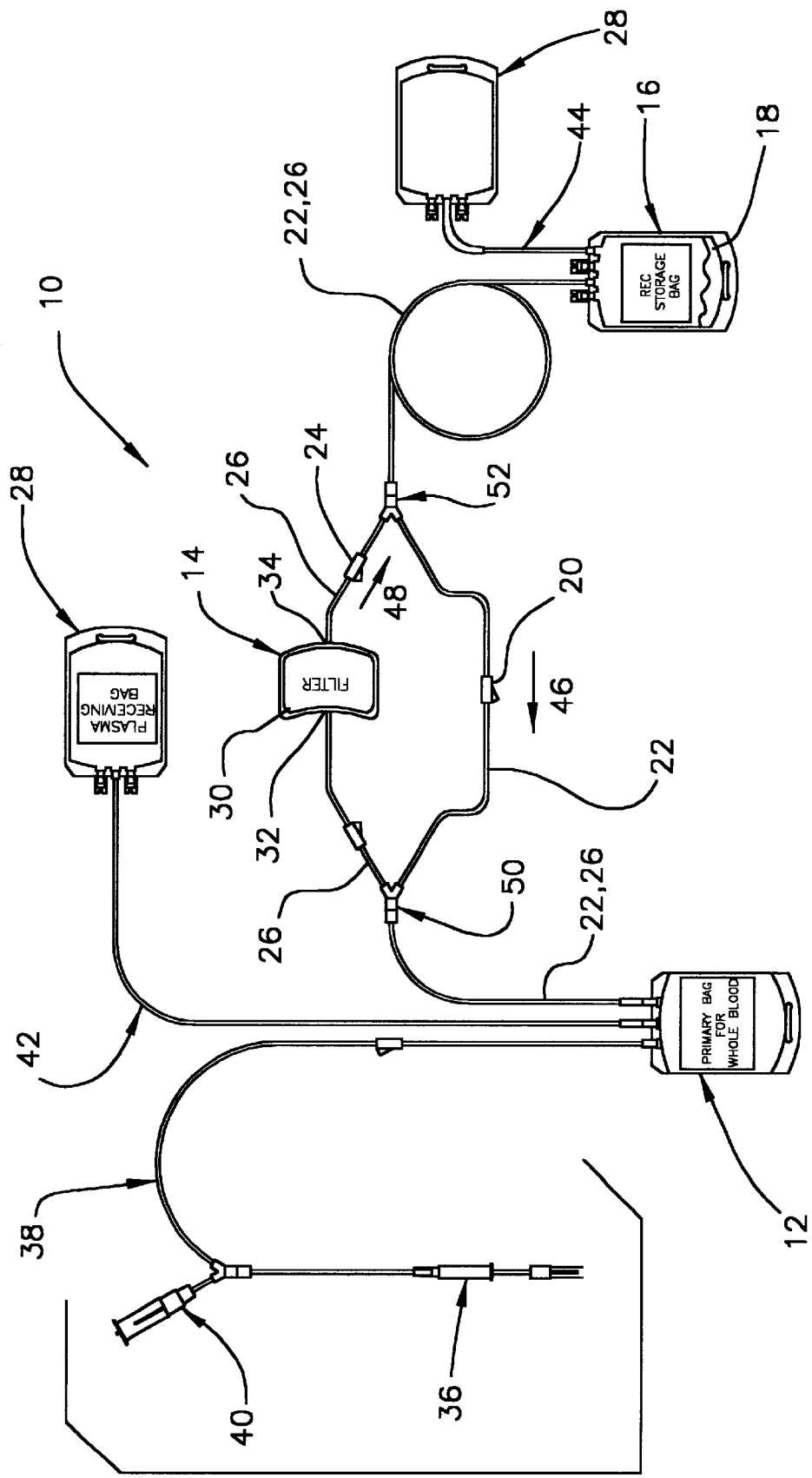
FIG. 1 is a schematic view of multiple embodiments of an in-line filtration system in accordance with the features of the present invention.

Referring now to the drawings (FIG. 1), there are depicted various embodiments of the invention comprising an in-line biological liquid filtration system 10. In an embodiment of the invention, a puncture assembly 11 is in fluid flow communication with a collection container 12 via third fluid path 38. The puncture assembly generally comprises a conventional needle member 36 for drawing blood or biological liquid from a human and collecting the drawn liquid in the container 12. The container 12 is preferably empty or substantially free of a remote additive solution (described herein) before the system is put in use. However, the container 12 preferably has a clinically sufficient amount of a conventional anti-coagulant therein to mix with the collecting blood once collection commences. The clinically sufficient amount could be placed within container 12 during the manufacture of the system or it could comprise part or all of the additive solution located in container 16 being introduced into container 12 before blood collection commences.

Located along the path 38 between the needle member and the container 12 is preferably also included a conventional sampling member 40. The sampling member 40 is in fluid flow communication with the path 38 and provides a sterile sampling site for sampling liquid drawn from the human.

A filter 14 is downstream of the collection container 12 and in fluid flow communication therewith. The filter comprises a filter housing 30 which includes an inlet 32 and an outlet 34. A gravity operable filtration media is located in the housing for filtering undesired matter from the biological liquid. Preferably the filtration media comprises a leukocyte media for filtering at least leukocytes from the biological liquid when it filters therethrough. The filter 14 preferably comprises the filtration device disclosed in U.S. Pat. No. 5,472,605 issued Dec. 5, 1995, or the filtration device disclosed in U.S. application Ser. No. 08/812,717, filed Mar. 6, 1997, U.S. Pat. No. 6,010,633, both which are incorporated by reference herein.

A storage container 16 is downstream of the filter. Within the storage container is preferably located an additive solution 18. Such a solution serves to enhance the storage life of biological liquid and also is an anti-coagulant for mixing with the biological liquid before it is filtered. In addition to housing the additive solution remotely from the collection container, on a. post-filtered side of the system, the storage container is adapted to receive filtered biological liquid for longer term storage therein. Although any variety of anti-coagulants could be utilized, an anti-coagulant contemplated to produce favorable results with this invention is Citrate Phosphate Dextrose, commonly known as CPD, and in a liquid form.

The container 16 is in fluid flow communication with the filter and the collection container via fluid path 22, 26. As shown in FIG. 1, the paths 22 and 26 have common fluid paths between the inlet 32 and the collection container and between the outlet 34 and the storage container.

Fluid path 22 preferably includes an automatic control member or first control member 20. The member 20 automatically substantially restricts the flow of liquid therethrough when liquid passes in the opposite direction of 46, i.e., from the collection container to the storage container. In this way, any flow of liquid from the collection container is automatically substantially directed to pass through the filter 14 in the direction 48. Conversely, any flow of additive solution from the storage container is automatically permitted to flow through control member 20 in the direction of 46, en route to the collection container. It is preferred that control member 20 be located as near as possible to junction 50 in order to minimize the amount of fluid left in the system during filtration.

Fluid path 26 also preferably includes an automatic control member or second control member 24. The member 24 automatically substantially restricts the flow of additive solution therethrough when solution passes in the opposite direction of 48, i.e., from the storage container to the collection container. In this way, any flow of solution from the storage container is automatically substantially directed through the fluid path 22 in the direction of 46 and thus bypassing filter 14. It is preferred that the control member 24 be located as near as possible to junction 52 in order to maximize the amount of additive solution conveyed from the storage container to the collection container during operation of the system.

As shown in the drawings, control members 20, 24 are configured and operate such that additive solution can be conveyed from the storage container 16 along fluid path 22, 26, to path 22 in the direction of 46, to path 22, 26, and into the collection container 12. Then, biological fluid or a mixture of fluid and additive solution can be conveyed along fluid path 22, 26, to path 26 including filter 14 in the direction of 48, to path 22, 26, and into the storage container 16. Automatic control members 20 and 24 preferably comprise check valves for use in-line for biological liquid comprising blood or blood products and for additive solution. Such a check valve could be like that depicted in FIG. 2, or any other conventional check valve structure. Check valves for members 20 and 24 can be similar, but only differing in their orientation within the system. For example, a check valve for member 20 and/or 24 could comprise a ball 55 and a spring 57 in a housing 59. Flow of fluid in the direction 46 is permitted, but not reverse flow. Alternatively, as depicted in FIG. 3, a check valve for member 20 and/or 24 could comprise a flap 61 in a housing 63. At least the flap, and also the housing if desired, would have a resilient characteristic where the flap would generally be forced against a seat ring to prevent fluid from flowing opposite direction 46 but flow in direction 46 as desired.

Figure 4:
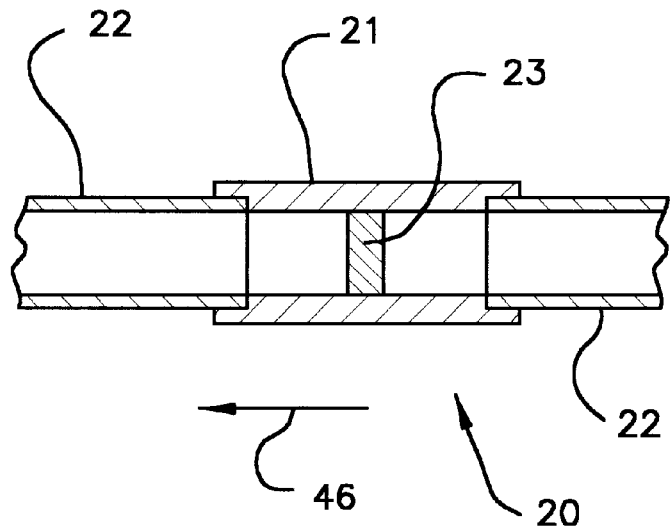
FIG. 4 is an enlarged cross-sectional view of a portion of the schematic shown in FIG. 1, here showing the details of a control member as a red cell barrier.

In another aspect, referring to FIG. 4, the invention may include the control number 20 comprising a red cell barrier. Preferably, the barrier will be located in fluid path 22. The barrier includes any conventional red cell barrier membrane 23 within a conventional housing 21 that together will serve to allow any liquid (e.g., additive solution, biological liquid, etc.) to pass there through but will not allow red blood cells that may be in the liquid to pass there through. Also, preferably, once the red cell barrier membrane is wetted by any liquid the membrane may not allow gas to pass there through. In FIG. 4, the red cell barrier membrane 23 is hermetically sealed by, to or within the tubing housing 21 by conventional means so as to not allow any liquid passing through the fluid path 22 to pass around the membrane and not through the membrane if the liquid desires to reach the opposite side of the membrane. For example, red cell barrier membrane 23 may comprise any conventional material known to be biocompatible and hemocyte compatible and having a pore size of less than 0.5 micron, and preferably less than 0.2 microns and most preferably less than 0.1 micron, in order to act as the red cell barrier desired here.

Figure 2:
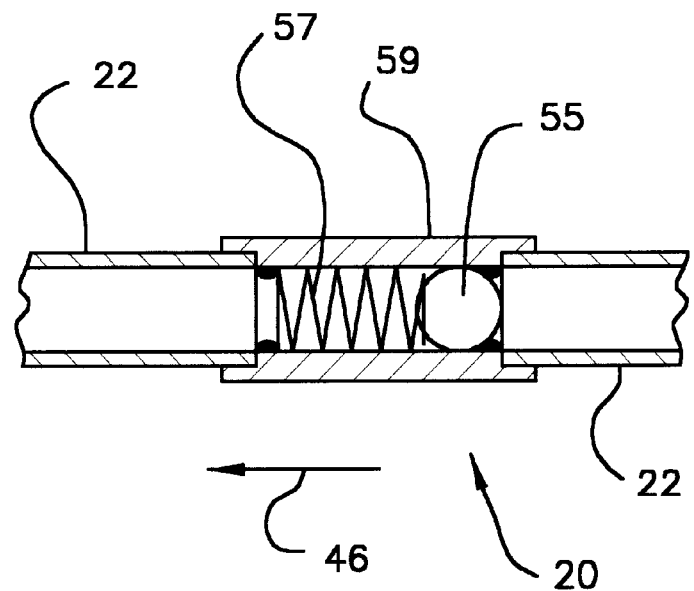
FIG. 2 is an enlarged cross-sectional view of a portion of the schematic shown in FIG. 1, here showing the details of a preferred control member as a check valve.
Figure 3:
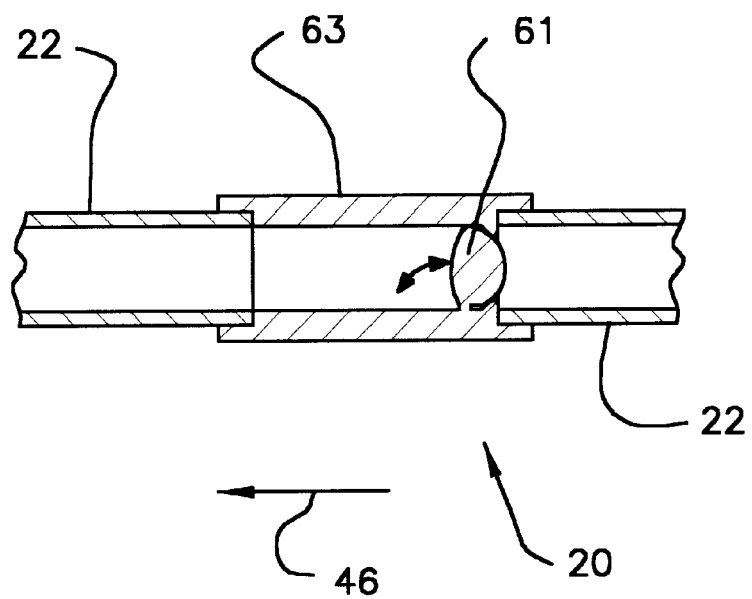
FIG. 3 is an enlarged cross-sectional view of a portion of the schematic shown in FIG. 1, here showing the details of an alternative preferred control member as a check valve.
Figure 5:
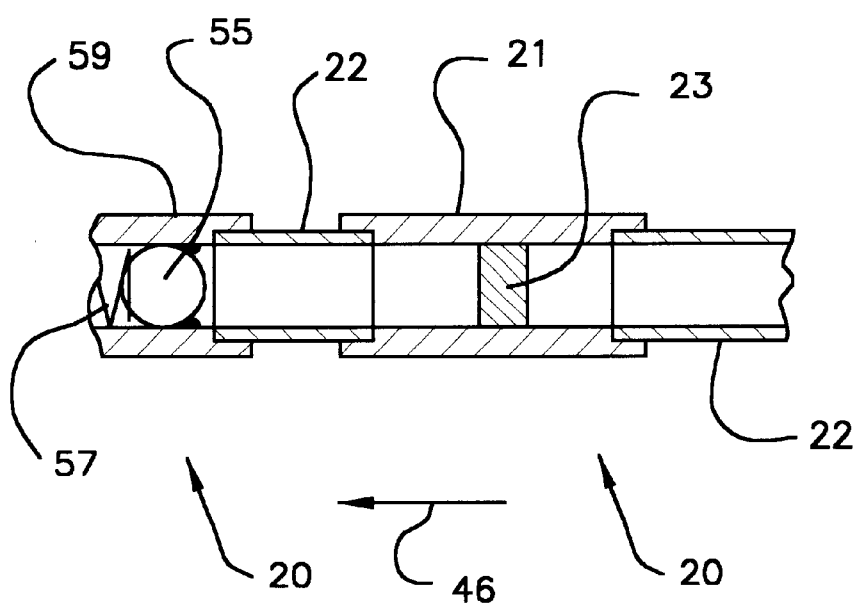
FIG. 5 is an enlarged cross-sectional view of a portion of the schematic shown in FIG. 1, here showing the details of an alternative control member as a red cell barrier and a check valve.

FIG. 5 discloses yet an alternative embodiment of the red cell barrier in combination with a check valve, such as the valves shown in FIGS. 2 and 3. It is further understood that the red cell barrier housing 21 and. the check valve housing (59 or 63) could be separate, as shown in FIG. 5, or one unified housing as would be known to do by one of ordinary skill in the art. The control member 20 could comprise the red cell barrier alone, the check valve alone, or a combination of both. Preferably, control member 20 will comprise at least the check valve and when it comprises both, the red cell barrier membrane 23 will be located downstream of the check valve ball 55 or flap 61.

Another embodiment of the invention, again referring to FIG. 1, may include one or more second storage container 28. Depending on the desired use for such a container, as described further hereinafter, the container may be in fluid flow communication with the collection container 12 and/or filter 14, e.g. via fourth fluid path 42, on a pre-filtered side of the system. Alternately, container 28 may be in fluid flow communication with the filter 14 and/or the storage container 16, e.g. via fifth fluid path 44, on the post-filtered side of the system.

The filtration system described herein includes several components and is preferably a "closed" in-line sterile system, as "closed" is generally understood in the art. The fluid paths 22, 26, 38, 42 and 44 preferably comprise a conventional tubing, as is used in biological liquid systems, to interconnect respective components and provide paths for fluid flow communication therebetween. The containers 12, 16 and 28 preferably comprise conventional flexible bags or containers for the collection and storage of biological liquids.

The system may comprise a number of modules wherein tubing is connected together via tubing connectors or the like to comprise a complete in-line closed system. However, to best maintain the integrity of a closed sterile system from assembly through end use, it is preferred that the system comprise one integrally connected assembly. Thus, preferably all components are integrally assembled in a sterile environment, packaged together in a sterile packaging, and ready for use as an assembled unit.

Another feature of the invention comprises a process for filtering biological liquid in the system 10. For example, one embodiment of the process comprises a first step of collecting the biological liquid or blood in the collection container 12. Preferably, the collecting comprises withdrawing blood from the donor by the puncture assembly 11 and conveying the liquid to the collection container by convention means such as gravity and a height differential between the puncture assembly and the collection container. Additionally, the biological liquid may be sampled after it is withdrawn from the human.

Next, the additive solution 18 is conveyed into the collection container, preferably by the force of gravity wherein the storage container is located above the collection container such as by hanging the storage container and connected filter above the collection container. Automatic control member 24 automatically restricts the additive solution to fluid path 22 in the direction 46 substantially bypassing the filter 14 as the additive solution is conveyed to the collection container.

A further step comprises then conveying the biological liquid and the additive solution comprising a mixture into the storage container. Automatic second control member 20 automatically restricts the mixture to second fluid path 26 in the direction 48 substantially passing through the filtration media when the mixture is conveyed into the storage container. In this way undesired matter, e.g. leukocytes, are filtered from the blood before the mixture enters the storage container. This step is preferably performed by the operation of gravity wherein the storage container is located below the collection container and the filter, such as by hanging the collection container and connected filter above the storage container. Finally, the tubing interconnecting the various components is sealed and cut, the storage containers are prepared for later use and the other components are discarded.

Another embodiment of the process comprises separating the blood into blood products before conveying the additive solution from container 16 into the collection container and mixing the additive solution with the liquid in that container.

Preferably, once blood is drawn from the human then the third fluid path 38 is sealed closed and the puncture assembly 11 is disconnected-from the system.

Next, the blood is separated into blood products, e.g., blood cells, plasma or platelets, using conventional separation means, e.g. a centrifugal apparatus and process. During separation, it is preferred that the whole system (minus the puncture assembly previously disconnected) be able to be subject to separation forces, namely, centrifugal forces. Further, the system should be able to be housed in a centrifuge or like device without having to separate any of the remaining components until filtration is complete. The system of this invention meets these requirements.

Once the blood has been separated, one or more blood product is then conveyed from the collection container into the second storage container 28 via the fourth fluid path 42. As desired, further separation of the remaining blood and blood products may be performed in a manner similar to the above. Then, additional blood product may be conyeyed out of the collection container into other storage containers 28 prior to conveying the additive solution into the collection container. Finally, the additive solution is conveyed into the collection container and mixed with the remaining liquid and filtration is performed as discussed previously.

Yet another embodiment of the process comprises conveying blood or blood product into a second storage container 28 on the post-filter side of the system. In this embodiment the second storage container is preferably in fluid flow communication with the storage container as shown. However, it should be understood that the storage container 28 could be located in direct fluid flow communication with the filter 14, such as via fluid path 22 or the common portion of fluid path 22,26 on the postfilter side of the system. In this way select filtering of separated blood products can be performed ahead of others and the filtered liquid collected in one or more storage containers on the post-filtered side of the system. Gravity is also the preferred conveying force where an appropriate height differential for the components is employed. Alternatively, as well as anytime the force of gravity is the preferred conveying means for the system, external pressure could be applied to the containers of the system to convey liquid by means of pressure differentials, e.g, from a higher pressure part of the system to a lower pressure part of the system.

Still another embodiment of the process comprises operating the system when the control member 20 comprises the red cell barrier alone or in combination with the check valve. When the control member 20 comprises the combination of the check valve and the red cell barrier, the system operates similar to that described previously when the control member 20 comprised the check valve alone. A difference now is that once the mixture passes into the storage container 16, red cells within the mixture cannot then be passed back through the fluid path 22 because the red cell barrier, including the red cell barrier membrane 23, prohibits of passage of red cells there through. Additionally, as preferred, because the red cell barrier membrane 23 is wetted by the additive solution when the additive solution is conveyed from the storage container 18 to the collection container 12 to make the mixture, gas within the system downstream of the red cell barrier membrane 23 is not allowed to pass there through any time after the membrane 23 is wetted.

If the control member 20 comprises only the red cell barrier, and not in combination with the check valve, the system operates similar to the previous description when the control member 20 comprised the check valve alone. A difference now is that a tubing clamp or other conventional means for closing the fluid path 22 must be employed so that when the mixture is conveyed from the collection container 12 through fluid path 26 and the filter 14, it is prevented from also passing through fluid path 22 and bypassing the filter in a direction opposite of 46. That is, the red cell barrier membrane 23 will only prohibit the flow of red cells and not other liquid components such as additive solution, white blood cells, and other biological liquid components. Once the mixture has passed through fluid path 26, including the filter 14, and is collected within the storage container 16, the red cell barrier membrane 23 functions, and the system operates, similar to that as just described when the control member 20 comprises the combination of the red cell barrier and the check valve.

As various possible embodiments may be made in the above invention for use for different purposes and as various changes might be made in the embodiments above set forth, it is understood that all of the above matters here set forth or shown in the accompanying drawings are to be interpreted as illustrative and not in a limiting sense.

What is claimed is:

1. An in-line biological liquid filtration system comprising:

a collection container for receiving said biological liquid;

filter means located downstream of the collection container and in fluid flow communication therewith;

a storage container for receiving filtered biological liquid located downstream of the filter means, said storage container in fluid flow communication with the filter means and with the collection container, wherein the fluid flow communication between the storage container and the collection container comprises at least first and second flow paths, the first flow path passing through the filter mean, and the second flow path substantially bypassing the filter means;

an additive solution located in the storage container; and automatic control means for automatically directing the flow of biological liquid from the collection container through the filter means and for automatically restricting the flow of additive solution from the storage container and into the filter means, wherein the automatic control means comprises a first automatic control member chosen from a check valve, a red cell barrier or a combination of a check valve and a red cell barrier, that automatically directs the flow of additive solution from the storage container to the collection container along said second flow path.

2. The in-line biological liquid filtration system of claim 1, wherein the automatic control means further comprises a second automatic control member that automatically directs the flow of biological liquid from the collection container to the storage container through the filter means along the first flow path.

3. The in-line biological liquid filtration system of claim 2, wherein the second automatic control member automatically restricts the flow of additive solution from the storage container to the collection container along the first flow path.

4. The in-line biological liquid filtration system of claim 3, wherein the second automatic control member comprises a check valve.

5. The in-line biological liquid filtration system of claim 1, wherein the biological liquid is blood or a blood product.

6. The in-line biological liquid filtration system of claim 5, wherein the filter means comprises a filter housing having an inlet and an outlet and a leukocyte filter located therein for filtering the biological liquid.

7. The in-line biological liquid filtration system of claim 1, wherein the filter means is a leukocyte filter.

8. The in-line biological liquid filtration system of claim 1, wherein one or both of the collection and storage containers are flexible containers.

* * * * *

UNITED STATES PATENT AND TRADEMARK OFFICE
CERTIFICATE OF CORRECTION

PATENT NO.   : 6,495,039 B1
DATED        : December 17, 2002
INVENTOR(S)  : Lee et al.

It is certified that error appears in the above-identified patent and that said Letters Patent is hereby corrected as shown below:

<u>Column 7,</u>
Line 36, delete the word "mean" and insert -- means --

Signed and Sealed this

Seventeenth Day of June, 2003

JAMES E. ROGAN
*Director of the United States Patent and Trademark Office*